(12) United States Patent
Walker et al.

(10) Patent No.: US 8,870,819 B2
(45) Date of Patent: *Oct. 28, 2014

(54) METHOD FOR A CENTRAL VENOUS LINE CATHETER HAVING A TEMPERATURE CONTROL SYSTEM

(71) Applicant: Zoll Circulation, Inc., Sunnyvale, CA (US)

(72) Inventors: Blair D. Walker, Mission Viejo, CA (US); Scott M. Evans, Santa Ana, CA (US); David P. Balding, Mission Viejo, CA (US); Peter Barker, Oceanside, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/652,787

(22) Filed: Oct. 16, 2012

(65) Prior Publication Data

US 2013/0046232 A1 Feb. 21, 2013

Related U.S. Application Data

(63) Continuation of application No. 12/015,125, filed on Jan. 16, 2008, now Pat. No. 8,313,461, which is a (Continued)

(51) Int. Cl.
*A61F 7/12* (2006.01)
*A61M 31/00* (2006.01)

(Continued)

(52) U.S. Cl.
CPC .............. *A61F 7/12* (2013.01); *A61M 25/02* (2013.01); *A61M 2205/36* (2013.01); *A61F 2007/0054* (2013.01); *A61M 25/0032* (2013.01); *A61M 2025/0036* (2013.01); *A61F 7/123* (2013.01); *A61M 25/10* (2013.01); *A61M 2025/1013* (2013.01); *A61F 2007/126* (2013.01); *A61M 1/369* (2013.01); *A61M 5/44* (2013.01); *A61B 2017/00084* (2013.01); *A61M 2205/366* (2013.01); *A61M 25/003* (2013.01); *A61M 25/002* (2013.01); *A61M 25/1011* (2013.01)
USPC ............... 604/113; 604/96.01; 604/103.01

(58) Field of Classification Search
USPC ............ 604/113–114, 101.01–103.14, 96.01
See application file for complete search history.

(56) References Cited

U.S. PATENT DOCUMENTS 4,941,475 A * 7/1990 Williams et al. ............... 600/505
5,135,474 A * 8/1992 Swan et al. ........................ 604/8

(Continued)

*Primary Examiner* — Rebecca E Eisenberg
(74) *Attorney, Agent, or Firm* — John L. Rogitz

(57) ABSTRACT

A kit of parts comprises a system and instructions for use for controlling patient temperature which uses a central venous line catheter having a heat exchange element. The central venous line catheter is provided with one or more lumens for providing access to the central blood supply of the patient, and with additional lumens for communicating heat exchange fluid to the heat exchange element. Heat exchange fluid temperature is controlled through a feed back loop in which patient temperature is sensed and used to control a temperature control unit comprising a heating device and/or a cooling device in heat exchange relationship with the heat exchange fluid. A tubing set transports the heat exchange fluid between the central venous line and the temperature control unit, with a pump serving to circulate the fluid in a closed fluid circuit in the system.

8 Claims, 3 Drawing Sheets

Related U.S. Application Data continuation of application No. 09/939,239, filed on Aug. 24, 2001, now Pat. No. 8,128,595, which is a continuation of application No. 09/671,114, filed on Sep. 28, 2000, now abandoned, which is a continuation-in-part of application No. 09/253,109, filed on Feb. 19, 1999, now abandoned, which is a continuation-in-part of application No. 09/063,984, filed on Apr. 21, 1998, now Pat. No. 6,126,684.

(51) Int. Cl.
*A61M 37/00* (2006.01)
*A61M 39/00* (2006.01)
*A61M 25/02* (2006.01)
*A61F 7/00* (2006.01)
*A61M 25/00* (2006.01)
*A61M 25/10* (2013.01)
*A61M 1/36* (2006.01)
*A61M 5/44* (2006.01)
*A61B 17/00* (2006.01)

(56) References Cited

U.S. PATENT DOCUMENTS 5,474,533 A * 12/1995 Ward et al. .................. 604/26
6,338,727 B1 * 1/2002 Noda et al. ................. 604/113

* cited by examiner

US 8,870,819 B2

METHOD FOR A CENTRAL VENOUS LINE CATHETER HAVING A TEMPERATURE CONTROL SYSTEM

CROSS-REFERENCE TO RELATED APPLICATIONS

This application is a continuation of U.S. patent. application Ser. No. 12/015,125, filed Jan 16, 2008, now U.S. Pat. No. 8,313,461, which is a Continuation of pending prior application Ser. No. 09/671,114 entitled Kit of Parts Including a Central Venous Line Catheter Having a Temperature Control System, filed on Sep. 28, 2000, which is a Continuation-in-part of U.S. patent application Ser. No. 09/253,109 entitled Central Venous Line Catheter Having Temperature Control System, filed Feb. 19, 1999, which is a Continuation-in-part of U.S. patent application Ser. No. 09/063,984 entitled Indwelling Heat Exchange Catheter and Method of Using Same, filed Apr. 21, 1998, now issued as U.S. Pat. No. 6,126,684, the disclosures of which are incorporated herein by reference in their entirety. Priority is claimed to all of the above documents.

BACKGROUND OF THE INVENTION

1. Field of the Invention

The invention relates to catheters used for access to the central venous blood supply of a patient.

2. Description of Related Art

Catheters such as central venous line catheters are typically used in ICU (intensive care unit) patients, particularly in those patients who have suffered a stroke or other brain traumatic event. The central venous line catheters are typically about 8.5-12 French in size and consist of a soft, flexible multi-lumen structure extending 8-12 inches. They are usually introduced through the subclavian or jugular vein, and less preferably in the femoral vein of the patient, serving to provide the caretaker with easy and convenient access to the patient's central blood supply via the central venous system. In this manner general access to the central blood supply is gained, enabling for example delivery of drugs, infusion fluids or nutrition, along with the gathering of patient blood for blood gas analysis and the like.

In many patients, such as ICU patients, fever is a common occurrence. Fever is particularly likely in neuro-ICU patients, and its onset can exacerbate detrimental effects in the brain. Conventional therapies to control fever include treatment with acetaminophen (Tylenol), cooling blankets, ice water bladder lavages, and ice baths. All of these approaches to cooling a patient require excessive time to cool the patient. Moreover, prior methods do not provide for precise control of patient cooling. As recognized herein, to optimize the advantage of cooling a patient, it is important to cool the patient relatively quickly in a controlled fashion.

Recognizing the above-mentioned deleterious effects of fever in ICU patients and the insufficiencies of present temperature control methods and devices, the present assignee has disclosed, in co-pending patent application Ser. Nos. 09/133,813 and 09/063,984, indwelling catheters that can be implanted in the body of a patient to remove heat from the blood supply of the patient. The indwelling catheters of the above-referenced applications are disposed in a heat exchange relationship with the blood supply, and a coolant is circulated through the catheters in a closed loop. These catheters lower the temperature of body tissue and, as mentioned above, can thereby improve the patient's medical outcome.

As understood by the present invention, the advantages of the above-referenced cooling catheters can be implemented into a central venous catheter configuration. As mentioned above, central venous catheters are commonly used in many ICU patients, including neuro-ICU patients, and with these combined recognitions, the present invention understands that it would be advantageous to provide a central venous catheter with the additional capability of cooling a patient. In doing so, the present invention satisfies the goals both of conventional central venous catheters as well as providing a means for effectively and precisely managing patient temperature in a single device.

BRIEF SUMMARY OF THE INVENTION

The present invention overcomes the deficiencies of the prior art by providing a kit of parts comprising a central venous line catheter adapted to actively exchange heat with the body of the patient to thereby raise or lower body temperature as required, along with instructions for proper use of the central venous line catheter. The central venous line catheter is provided with a heat exchange element disposed in heat exchange relationship with the blood of the patient. The heat exchange element houses a circulating fluid therein, with the fluid being automatically cooled or warmed exteriorly of the patient's body in accordance with a patient temperature feedback scheme.

By supplementing the known functions of a central venous line catheter with the function of cooling or warming the patient's blood, the present invention takes advantage of existing access to the venous system and a single incision, reducing the risk of additional complications. The access, typically through the subclavian, jugular or femoral veins, is to the central blood supply, via the central venous system, and is therefore particularly expedient, permitting efficient cooling or warming of patient body temperature. The term central venous system generally relates to the portion of the venous system which returns blood to the right heart, including the inferior and superior vena cava. A particular advantage of the invention is that the cooling function is performed efficiently in tandem with a procedure which is known to be likely attended by fever, thus anticipating such fever and facilitating its control. The heat exchange relationship between the system and the central venous system of the patient can be maintained for a prolonged duration—for example, from about one hour to about twenty-nine days.

The central venous line catheter in accordance with the invention comprises a tubular structure defining a plurality of lumens. At least two of these lumens convey heat exchange fluid to a heat exchange element disposed at a distal, implantable end of the central venous line catheter, while the rest of the lumens serve to provide access to the central blood supply of the patient. The heat exchange element is in fluid communication with a temperature control module via a tubing set which conveys the heat exchange fluid between the components. The temperature control unit, comprising a cooling and/or a heating device, operates in conjunction with a temperature controller to heat or cool the heat exchange fluid depending on a sensed temperature of the patient.

In a less preferred embodiment, the heat exchanger element of the present invention can be made of metal such as steel, and it can assume an appropriate configuration, such as an accordion-like configuration.

The system of the invention operates to maintain patient temperature at a desired level. Any deviation from the desired level automatically triggers corrective action, such as circulating the cooled heat exchange fluid through the central venous line catheter to contend with the onset of fever. Additionally, the system is equipped with indicators which signal to the caretaker of the patient the sensed deviation, by for example sensing the increased workload of the system, in order to warn of adverse physiological changes besetting the patient.

The invention thus provides a system for controlling patient temperature using a central venous line catheter having a heat exchange element. The central venous line catheter is provided with one or more lumens for providing access to the central blood supply of the patient, and with additional lumens for communicating heat exchange fluid to the heat exchange element. Heat exchange fluid temperature is controlled through a feedback loop in which patient temperature is sensed and used to control a temperature control unit comprising a heating device and/or a cooling device in heat exchange relationship with the heat exchange fluid. A tubing set transports the heat exchange fluid between the central venous line and the temperature control unit, with a pump serving to circulate the fluid in a closed fluid circuit in the system.

BRIEF DESCRIPTION OF THE SEVERAL VIEWS OF THE DRAWING(S)

Many advantages of the present invention will be apparent to those skilled in the art with a reading of this specification in conjunction with the attached drawings, wherein like reference numerals are applied to like elements and wherein.

DETAILED DESCRIPTION OF THE INVENTION

Figure 1:
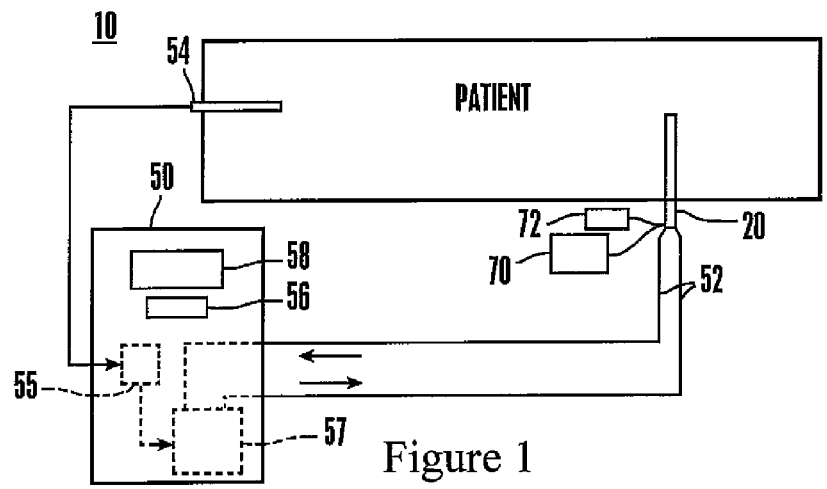
FIG. 1 is a schematic diagram showing a central venous line catheter temperature control system in accordance with the present invention.

FIG. 1 shows a temperature control system 10 in accordance with the invention. A central venous line catheter 20 providing access to the central blood supply of the patient is disposed in heat exchange relationship with the patient. Central venous line catheter 20 is provided with a circulating heat exchange fluid (not shown) whose temperature is automatically controlled in accordance with a feedback scheme in order to achieve a desired patient target temperature or temperature range. The feedback schemes involves sensing patient temperature using a probe 54 whose output is provided to a temperature controller 55 housed in a temperature control module 50. The temperature controller 55 determines whether the sensed temperature represents a deviation from the desired temperature or range and selectively activates a heat control unit 57 in order to heat or cool the heat exchange fluid depending on the direction of deviation. As described in more detail below, the central venous line catheter 20 is a multi-lumen device, with at least two of the lumens being dedicated to heat exchange fluid flow to and from a heat exchange element of the catheter. The other lumen(s) can have different uses, such as fluid infusion or drug delivery, or guidewire support, depending on the particular application. The preferred number of lumens is 3 to 5, although other numbers are contemplated.

Figure 2:
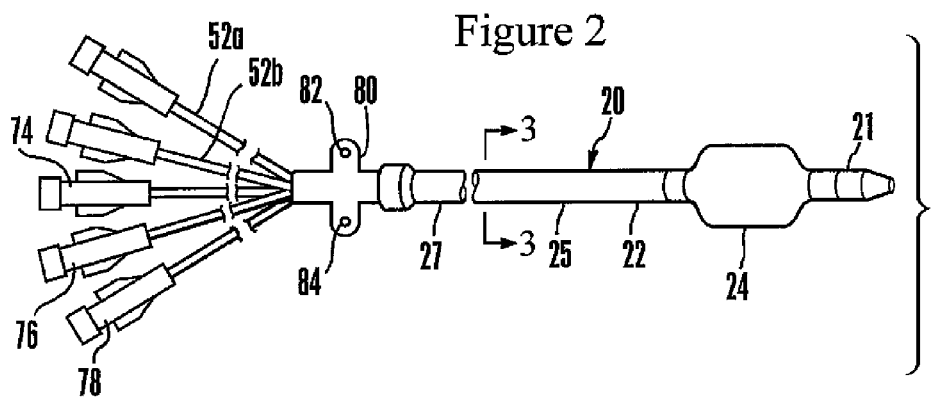
FIG. 2 is a schematic side elevational view of a central venous line catheter in accordance with the invention.
Figure 3:
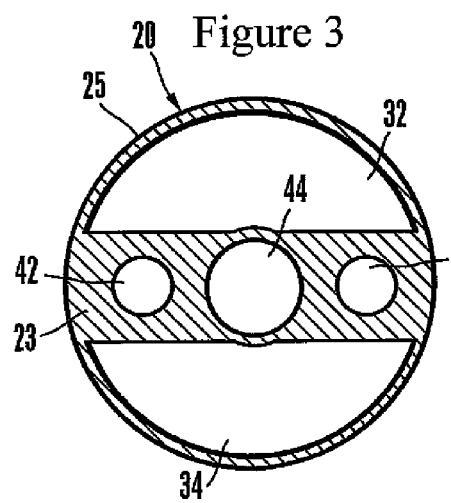
FIG. 3 is a schematic cross-sectional view taken along line 3-3 of FIG. 2.
Figure 4:
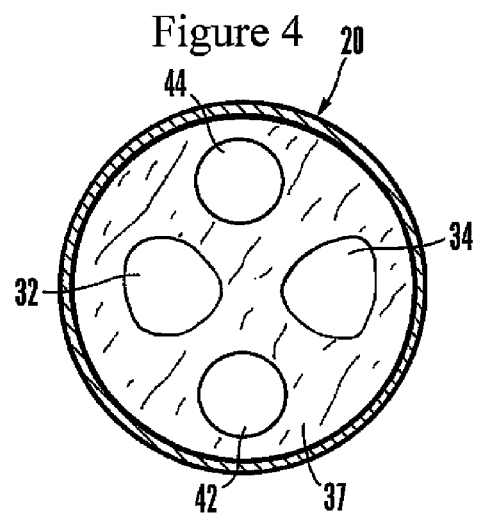
FIG. 4 is a schematic cross-sectional view of a preferred arrangement of a catheter in accordance with the invention.
Figure 5:
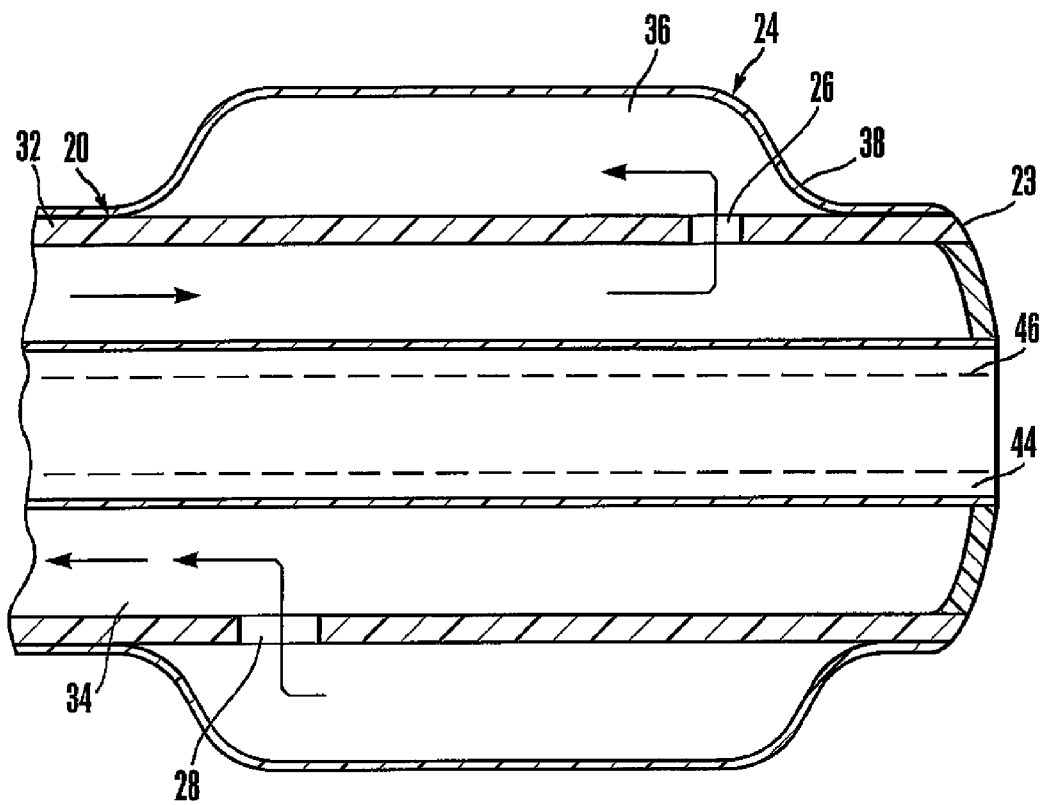
FIG. 5 is a schematic sectional view of the distal portion of the central venous line catheter of the invention.

FIGS. 2-4 show in more detail the central venous line catheter 20, which is a substantially elongate structure of generally cylindrical shape adapted for insertion into the body of a patient, preferably into the subclavian or jugular veins. Central venous line catheter 20 is formed of any known polymer material 23 defining its various lumens 32, 34, 42, 44 and 46. A preferred material is polyurethane, although other materials, such as nylon, polyethylene and PEBAX, can also be used. Considerations in selecting the appropriate material 23 include biocompatibility, flexibility, temperature change compatibility, and resistance to buckling.

At its distal, implantable end portion 22, catheter 20 is provided with a heat exchange element such as fluid-carrying inflatable balloon 24 that is radially disposed around the width of the catheter. Balloon 24 is disposed in the vicinity of flexible tip 21 and can be formed from a piece of sheet material 38 or extruded tubing formed into a molded balloon of the desired shape and size and then bound or otherwise fixed to the shaft 25 to form a cavity 36. As illustrated, balloon 24 is shown to have a significantly larger diameter than shaft portion 25 of the catheter. For example, it is contemplated that in some applications the diameter of the inflated balloon will be more than three times that of shaft 25. In one preferred embodiment, the balloon diameter is four millimeters to ten millimeters (4 mm-10 mm). Preferably, the diameter of the balloon is selected to be no more than 40%-60% of the diameter of a typical vena cava. It is to be appreciated that in some cases it may be desirable to maximize the dimension of the shaft 25 in order to facilitate heat exchange fluid flow. This will also minimize the volume of fluid in the balloon 24 and promote a more rapid heat exchange. It will be further appreciated that myriad balloon shapes can be utilized with the invention, including but not limited to spiral or fluted shapes, as disclosed in the aforementioned co-pending patent applications. The particular shape selected would depend on the application and the desired heat exchange and other characteristics. In one preferred embodiment, the balloon 24 is made of urethane, nylon, or PET and is thin-walled, i.e., the balloon 24 has a wall thickness of less than three mils, and more preferably less than one and one-half mils. Also the balloon 24 preferably is coated with an antimicrobial substance, as well as an anticlot substance, such as heparin.

It is to be understood that the balloon 24 can extend the entire length of the portion of the central venous catheter that is intubated in the patient. Typically, this length is about 15 cm. Under such circumstances, the diameter of the balloon need not be larger than the diameter of a conventional central venous catheter, e.g., the diameter of the balloon can be 12 French, 10 French, or even as small as 7.5 French. More broadly, the balloon diameter, when the balloon extends along the entire length of the intubated portion of the catheter, can be 5-13 French. In an arrangement where multiple balloons are used as detailed below, these balloons can cover the entire length of the intubated portion of the catheter. That is, two balloons of about 7.5 cm each can be used, or three 5 cm balloons, etc.

As can be seen more clearly with reference to FIGS. 3 and 4, a pair of lumens 32 and 34 are formed in catheter 20, with lumen 32 serving as an inflow channel supplying balloon 24 with heat exchange fluid which is circulated through the catheter 20, while lumen 34 serves as an outflow channel returning the heat exchange fluid from the balloon 24 to the catheter. The particular heat exchange fluid selected is preferably biocompatible to avoid harm to the patient in the event of inadvertent rupture. Candidate materials include sterile saline water and carbon dioxide gas, although other fluids having suitable viscosity, heat exchange and material compatibility characteristics can also be used. While less desired because it is not biocompatible, freon can alternatively be used.

Balloon 24 is in fluid communication with lumens 32 and 34 via a plurality of ports such as inlet port 26 and outlet port 28. Heat exchange fluid circulated in catheter 20 passes from lumen 32 into cavity 36 through inlet port 26, then out of cavity 36 to lumen 34 through outlet port 28. While in the cavity 36, the heat exchange fluid, which is remotely cooled outside the central venous line catheter 20, serves to provide a cold temperature fluid on the inner surface of the sheet-material 38 which forms the walls of balloon 24. With a body fluid, such as blood, flowing exteriorly of the balloon 24, heat transfer occurs across the sheet material 38, effectively cooling the body of the patient and countering the effects of a fever. To that end, inlet port 26 is positioned distally of outlet port 28.

Efficient heat transfer is also promoted by specific considerations regarding the cross-sectional shape of the lumens 32 and 34. Specifically, as can be seen from FIG. 3, the lumens 32 and 34 are designed to maximize the volume of fluid flowing therethrough. This is accomplished by providing the lumens with crescent cross-sectional shapes so as to occupy circumferentially a maximum arc length in the catheter 20. This volume maximization, however, may be at the expense of thermal efficiency since the crescent cross-sectional shapes provide greater surface area for undesirable heat exchange with the exterior of the catheter 20 in the shaft portion 25. To obviate this, the preferred cross-sectional shape, shown in FIG. 4, more effectively isolates lumens 32 and 34 from the exterior of catheter 20 by the structural material 37 of the catheter.

Figure 6:
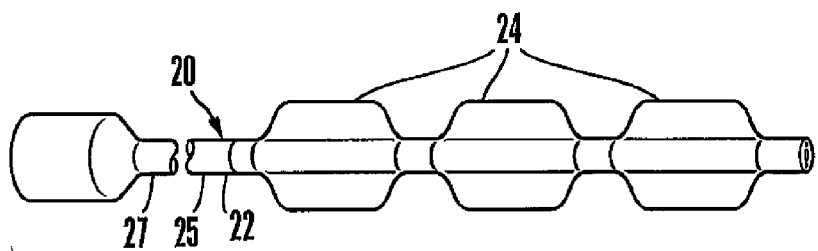
FIG. 6 is a schematic side elevational view of a central venous line catheter in accordance with a second embodiment of the invention.

In order to facilitate fluid flow in and out of cavity 36 of balloon 24, outlet port 28 can be made larger than inlet port 26 to reduce the resistance encountered by the heat exchange fluid as it exits the balloon 24. This relative size difference becomes particularly important when multiple balloons are provided in catheter 20 as is contemplated in accordance with an alternate embodiment of the invention. Specifically, although described in terms of a single balloon 24, it will be appreciated that several such balloons can be provided, disposed axially along the length of shaft 25, as shown in FIG. 6. One advantage of a multiple balloon configuration is that the flow and temperature of the heat exchange fluid can be more easily controlled along the entire length of the exchange region of the catheter 20. Realizing that the heat exchange fluid will be coolest prior to entering into heat exchange with the blood, and warmest after that heat exchange, one can advantageously control not only the velocity and volume of flow, but also the direction of flow within each of the balloons 24. Another advantage of a multiple balloon design is the ability of the catheter to bend and flex when placed in a curved vasculature.

Catheter 20 is also provided with two or three lumens 42, 44 and 46 in addition to lumens 32 and 34. Lumens 42, 44 and 46 can serve a multiplicity of functions, including infusion of drugs such as chemotherapy, fluids and nutrition, access to syringes for sampling, and accommodation of various sensors, such as thermistors to monitor the patient, thus generally providing access to the central blood supply as dictated by the particular application. Additionally, central lumen 44 may be made of a different diameter than side lumens 42 and 46 in order to better support a guidewire for instance. The lumens extend substantially the full length of catheter 20, from proximal end portion 27 to distal end portion 22. The number of lumens provided can be varied depending on the particular application.

Figure 7:
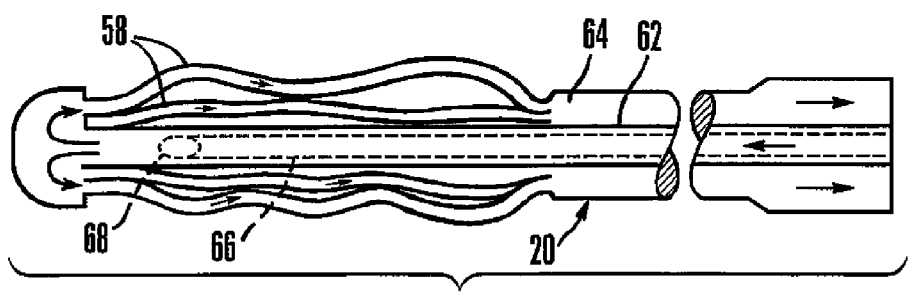
FIG. 7 is a schematic side elevational view of a central venous line catheter in accordance with a third embodiment of the invention.

It will also be appreciated that the heat exchange element does not necessarily need to be in the form of a balloon such as balloon 24. Rather, arrangements such as an array of flexible hollow fibers through which the heat exchange fluid is circulated can also be used, thus affording greater surface area for heat exchange interaction. Such an arrangement, along with other heat exchange element arrangements which can be used with the invention, is disclosed in the afore-mentioned co-pending patent application Ser. No. 09/133,813, herein incorporated by reference in its entirety. A hollow fiber heat exchange element configuration is shown in FIG. 7. Hollow fibers 58 receive fluid from inner heat exchange fluid lumen 62 and return this fluid to outer heat exchange fluid lumen 64 of catheter 20. Additional lumens such as lumen 66 are also provided to facilitate delivery of fluids and for other uses. An important advantage of a hollow fiber heat exchange element arrangement is that it enables communication between the inner lumens, such as lumen 66, and the blood anywhere along the length of the heat exchange element, via for example port 68.

With reference again to FIG. 1, and in cross-reference to FIG. 2, the catheter 20 operates in conjunction with a temperature control module 50. A tubing set 52 (FIG. 1) including coolant inlet and outlet fittings 52a, 52b (FIG. 2) conveys fluid between temperature control module 50 and catheter 20 in a closed fluid circuit through which the fluid is circulated, using known pumping means (not shown) such as for example a diaphragm pump, bladder pump, piston pump, peristaltic pump, etc. It is to be understood that the inlet and outlet fittings 52a, 52b establish pathways of fluid communication from the temperature control unit 57 to the lumens 32, 34, respectively of the catheter 20. A temperature controller 55, which may be a microprocessor having appropriate information storage memory (not shown), is provided in temperature control module 50 and receives patient temperature signals from probe 54. By controlling the input to a temperature control unit 57, which may be a cooling device and/or a heating device in heat exchange relationship with the cooling fluid, temperature controller 55 automatically adjusts the temperature of the heat exchange fluid according to a desired target temperature or temperature range. The target temperature or range can be entered using an input device such as keyboard 56. A display device such as LCD 58 displays various parameters to provide indications of system operation and/or patient condition.

Preferably, the target temperature is selected to be normal body temperature, and any deviation from this temperature, for example induced by the onset of fever, is sensed by the probe 54 and automatically corrected by the system of the invention. Temperature correction is effected by for example activating temperature control unit 57 of temperature control module 50. In cooling applications, temperature control unit 57 causes cooling of the circulating fluid and ultimately the cooling of the patient's core body temperature, which is monitored by probe 54. When normal temperature is achieved, the temperature control unit 57 can then be automatically switched off or its cooling effect reduced by the temperature controller 55. Suitable temperature control algorithms taking into account performance parameters of system components and system time constants are implemented by temperature controller 55 to effect accurate temperature control. For more expedient temperature control, module 50 may also be provided with a heating device as part of the temperature control unit 57, which heating device can also be automatically activated, using feedback from probe 54, to for example prevent overshooting the desired target temperature or range, or even to induce hyperthermia in some situations. It will be appreciated that probe 54 can be used to provide temperature feedback from any part of the patient's body, rectally for instance, or it can provide temperature information anywhere in the fluid circuit, which information can then be correlated to the patient's core temperature using known parameters such as heat conductivity of different portions of the system and patient data such as weight, height, age, etc. Additionally, more than one probe can be used to provide combinations of readings from he patient and/or from the system to improve accuracy under some circumstances.

In accordance with the invention, the feedback scheme can be used to maintain desired temperature conditions for a patient. Specifically, the system can be used to control any temperature deviations from an acceptable temperature range, which may be a normothermic range, whereby probe 54 will trigger cooling or heating of the patient's body depending on this sensed deviation from the predetermined range. Moreover, since this deviation is generally indicative of certain physiological activity of which the patient's caretaker should be apprised, the operation of the system can be used as an indication that this physiological activity is taking place. For instance, when the cooling operation of temperature control unit 57 is activated due to a rise in the patient's core body temperature, the system cooling activity, as reflected in the increased workload of the cooling componentry of the system, is then used to indicate to the caretaker, audibly or visibly using an alarm or other status indicator device (not shown) for instance, that the patient's body is attempting to enter a fever state. Appropriate measures can then be taken. Parameters other than workload can be used to provide this indication, such as the slope of the temperature feedback along with the sign of the slope. Alternatively, a direct indication of patient temperature as sensed by the probe 54 can be used. In this manner, use of the system for extended periods of time—for example, from about one hour to about twenty-nine or more days—is facilitated.

In cross-reference to FIGS. 1 and 2, in addition to being connected to the temperature control unit 57, the central venous catheter 20 is connected to one or more central venous components 70, 72 (only two venous components shown in FIG. 1 for clarity of disclosure) via respective fittings 74, 76, 78 as appropriate (FIG. 2) to establish communication between the central venous components 70, 72 and selected lumens 42, 44, 46 of the catheter 20. As intended by the present invention, the central venous components 70, 72 can be established by one or more of: drug infusion sources, blood receptacles for receiving blood through the catheter 20, a guide wire, etc.

Figure 8:
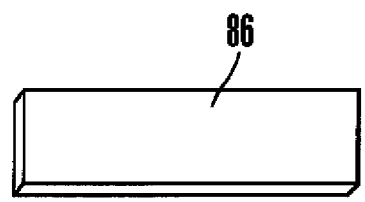
FIG. 8 is a perspective view of one embodiment of the present anchor.

Additionally, as best seen in FIG. 2, the catheter 20 includes an anchor configured for affixing the catheter 20 to the patient. More specifically, in one intended embodiment, the anchor is established by a suture fitting 80. The suture fitting 80 can be made integrally with the catheter 20, or it can be made as a separate plastic fitting and surroundingly engaged with the catheter 20. As shown, the suture fitting 80 includes two eyes 82, 84 through which sutures can be positioned and engaged with the patient's skin or with a bandage or tape or other structure that has been fastened to the patient. Alternatively, the present anchor can be established by a piece of tape 86, shown in FIG. 8, that can tape the catheter of the present invention to the patient. Yet again, the present anchor can include another fastening device such as a plate with adhesive surface that can be engaged with the patient, with the plate including structure configured for receiving the catheter of the present invention. As understood herein, an anchor is desirable in a central venous catheter to hold the catheter on the patient, because a central venous catheter typically is intended for prolonged indwelling.

Figure 9:
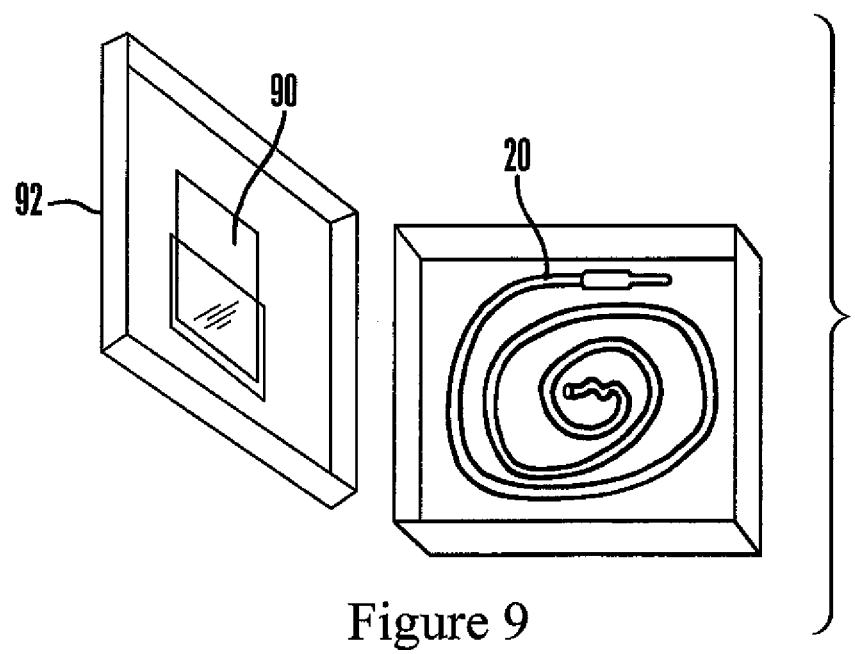
FIG. 9 is a perspective view of the kit of parts in accordance with the invention.

FIG. 9 is a schematic view of a kit of parts containing a central venous line catheter 20 and instructions for use 90 of same in accordance with the invention.

The kit of parts includes a package 92, having a box and a cover. The box housing the catheter 20. The cover including an interior. The instructions for use 90 mount on the interior of the cover and can be in the form of a booklet, or a card or label which may be adhered to the package 92 comprising the kit or otherwise associated with the central venous line catheter 20. The instructions for use 90 would be product-specific, depending on the particular model, size and application, and would instruct the operator of the catheter 20 on proper use of the catheter, for example including a description of the specifications of the catheter and the compatible equipment and materials with which its use is recommended. Warnings and precautions would also be included, along with contraindications, preparation procedures, and other medically important information. The following represents an exemplary of a set of instructions for use in accordance with the invention:

Device Description:

The COOL LINE™ Heat Exchange Catheter is a sterile, single use flexible 8.5F catheter designed for placement in the central venous circulation from an insertion site in the jugular, subclavian, or femoral veins. The COOL LINE™ catheter is to be connected to an ALSIUS single use disposable COOLGARD™ Tubing Set (supplied separately) and the COOLGARD™ System. A dilator and guidewire are required for the percutaneous insertion of the COOL LINE™ catheter. Two lumens are available for infusion, measuring-central venous pressure and sampling. Flow rates: Proximal port (blue) 1400 ml/hr. Distal Guidewire Port (brown) 2200 ml/hr. The COOL LINE™ blood contact surfaces are Duraflo® treated.

Indications for Use:

The ALSIUS COOL LINE™ Catheter in combination with the COOLGARD™ System is for reducing fever in neurointensive care unite patients.

Safety and Efficacy Consideration:

Product designed for single use only. Do not resterilize or reuse. Do not reinsert, once removed from patient. Do not alter the catheter in any way. Central venous catheterization should only be performed by well-trained personnel well versed in anatomical landmarks and safe technique. Personnel should also have knowledge of potential complications.

Warning: Do not allow catheter to be placed into right atrium or right ventricle. Placement in right atrium or right ventricle can result in severe patient injury or death.

Contraindications:

1. Bleeding diathesis.
2. Active sepsis.
3. Infection or active bleeding at the site-of catheter insertion.
4. Patients with no vascular access.

Warnings and Precautions:

1. Catheter should be placed via a jugular, subclavian, or femoral vein approach only.

2. Do not allow catheter to be placed into right atrium or right ventricle. If placed via the jugular or subclavian veins, catheter should be positioned so that the distal tip of catheter is in the superior vena cava above its junction with the right atrium and parallel to the vessel wall. X-ray examination should be used to ensure that the catheter is not in the right atrium or ventricle. The distal tip of the catheter should be positioned at a level above either the azygos vein or the carina of the trachea, whichever is better visualized.

3. If placed via the femoral vein, the catheter should be positioned so that the distal tip of catheter is in the inferior vena cava below its junction with the right atrium and parallel to the vessel wall.

4. Possible complications with central venous catheters include: atrial or ventricular perforation, cardiac tamponade, air embolism, catheter embolism, thoracic duct laceration, bacteremia, septicemia, thrombosis, inadvertent arterial puncture, hematoma formation, hemorrhage, nerve damage and dysrhythmias.

5. All Luer-Lock connections and covers must be securely tightened to prevent air embolism or fluid or blood loss.

6. Never use excessive force in moving the catheter or guidewire. If resistance is encountered, an x-ray should be performed to identify the reason for the resistance.

7. Passage of the guidewire into the right heart can cause dysrhythmias, right bundle branch block, vessel wall, atrial or ventricular perforation.

8. Use only sterile normal saline for catheter priming and as the circulating fluid in the catheter.

9. Catheter should be routinely inspected for flow rate, security of dressing, correct catheter position and for secure Luer-Lock connection. Use centimeter markings to identify if the catheter position has changed.

10. Only x-ray examination can ensure that the catheter tip has not entered the heart or no longer lies parallel to the vessel wall. If catheter position has changed, perform an x-ray examination to confirm catheter tip position.

11. For blood sampling, temporarily shut off remaining infusion ports through which solutions are being infused.

12. Alcohol and acetone can weaken the structure of the polyurethane material. Care should therefore be taken when infusing drugs containing alcohol or when using alcohol or acetone when performing routine catheter care and maintenance. Alcohol should not be used to doctor the catheter.

13. Use are when infusing drugs that may be affected by cool temperatures (as low as 4° C.).

14. Use of a syringe smaller than 10 ml to irrigate or declot an occluded catheter may cause intraluminal leakage or catheter rupture.

15. Do not infuse into the teal-green Luer-Lock connections.

16. Fever may have infectious and/or non-infectious causes in patients. Mitigation of fever as a sign of possible infection necessitates daily, meticulous assessment for other signs of infection.

More warnings and precautions are located in following instructions.

Materials Required:

| Quantity | Description |
| --- | --- |
| 1 | COOL LINE ™ Kit for percutaneous introduction |
| 1 | Bag of Normal Saline (1000 ml) |
| 1 | COOL LINE ™ Catheter |
| 1 | COOLGARD ™ Tubing Set |
| 1 | COOLGARD ™ System |

-continued

| Quantity | Description |
| --- | --- |
| 1 | Pack of Sterile Luer Caps (supplied with the COOLGARD ™ Tubing Set) |

Catheter Preparation and Insertion:

Use Sterile Technique.

1. Caution: Use jugular, subclavian, or femoral vein approach only.

2. Place patient in a slight Trendelenburg position as tolerated to reduce the risk of air embolism. If femoral approach is used, place patient in supine position.

3. Prep and drape puncture site as required.

4. Caution: Always prime catheter before it is inserted into patient.

5. Carefully remove catheter from package leaving on catheter membrane cover.

Catheter Preparation Procedure:

1. Remove caps from the inflow and outflow luer hubs. With the catheter cover in place, fill syringe (5 cc or larger) with sterile saline and attach syringe to female inflow luer hub.

2. Warning; Never inject positive pressure into the inflow hub with the outflow luer cap in place.

3. Gently inject saline through catheter until it begins to exit from outflow luer.

4. Using 5 cc or larger syringe, flush the distal and proximal infusion lumens with sterile saline. Clamp or attach injection caps to the proximal infusion lumen. Leave the distal luer uncapped for guidewire passage.

5. Remove catheter membrane cover. Inspect catheter to assure that air has been purged from the heat exchange membrane. Inspect the catheter for leaks.

6. Warning: Do not cut the catheter to alter length.

Catheter Insertion:

1. Obtain jugular, subclavian, or femoral venous access using standard percutaneous techniques. Access should be maintained with a 0.032" guidewire.

2. Caution: Do not use guidewire larger than 0.032" with the COOL LINE™ catheter.

3. Holding spring guidewire in place, remove introducer catheter. Precaution: Maintain a firm grip on the guidewire at all times.

4. Enlarge the cutaneous puncture site with cutting edge of scalpel positioned away from the guidewire. Warning: Do not cut guidewire. Use vessel dilator to enlarge site as required. Do not leave vessel dilator in place as an indwelling catheter to minimize risk of possible vessel wall perforation.

5. Thread tip of COOL LINE™ over guidewire. Maintain a sufficiently firm grip on the guidewire during catheter insertion. Grasping near skin, advance catheter into vein with a slight twisting motion.

6. Using centimeter marks on the catheter as positioning reference points, advance catheter to final indwelling position.

7. Hold catheter at desired depth and remove guidewire. If resistance is encountered when attempting to remove the guidewire after catheter placement, the guidewire may be kinked about the tip of the catheter. If resistance is encountered, withdraw the catheter relative to the guidewire about 2-3 cm and attempt to remove the guidewire. If resistance is again encountered remove the guidewire and catheter simultaneously.

8. Caution: Do not apply undue force to the guidewire.

9. Verify that the guidewire in intact upon removal.

10. Check lumen placement by attaching a syringe to the distal and proximal infusion luer hubs and aspirate until a free flow of venous blood is observed. Connect infusion luers to appropriate Luer-Lock line(s) as required. Unused infusion port(s) may be "locked" through the injection cap(s) using standard hospital protocol. Slide clamps are provided on the tubing to occlude flow through the infusion lumens during line and injection cap changes. Precaution: To minimize risk of damage to the tubing from excessive pressure, each clamp must be opened prior to infusing through that lumen.

11. Caution: Do not clamp or occlude inflow or outflow lines. This can cause line blockage and possible failure.

12. Secure and dress catheter temporarily.

13. If subclavian or jugular access is used, verify catheter tip position by chest x-ray immediately after placement. X-ray exam must show the catheter located in the right side of the mediastinum in the SVC with the distal end of the catheter parallel to the vena cava wall. The catheter distal tip must be positioned at a level above either the azygos vein or the carina of the trachea, whichever is better visualized. If the catheter tip of malpositioned, reposition and reverify.

14. If femoral access is used, X-ray examination must show the catheter located in the IVC with the distal end of the catheter parallel to the vena cava wall. If the catheter tip is malpositioned, reposition and reverify.

15. Proximal radiopaque marker indicates proximal end of balloons to ensure that balloons reside completely in vessel. If catheter is malpositioned, reposition and reverify.

16. Secure catheter to patient. Use juncture hub side wings as primary suture site.

17. The Alsius suture tab and clip can also be used as an additional attachment point. Assure that catheter body is secure and does not slide.

18. Caution: Do not suture directly to the outside diameter of the catheter to minimize the risk of cutting or damaging the catheter or impeding catheter flow.

19. Maintain the insertion site with regular meticulous redressing, using aseptic technique.

20. Record on the patient's chart the indwelling catheter length using the centimeter marks on the catheter shaft as reference. Frequent visual reassessment should be made to ensure that the catheter has not moved.

21. Attach a primed Tubing Set to COOL LINE™ Heat Exchange Catheter by connecting the male luer of the tubing set to the green female inflow luer of the COOL LINE™ catheter (labeled "inflow") and the female luer of the tubing set to the green male outflow luer of the COOL LINE™ catheter (labeled "outflow"). Assure that a sufficient amount of sterile saline is present at the ends of the hubs to make an air free connection. Refer to COOLGARD™ manual for details on COOLGARD™ operation.

22. Warning: Failure to connect the Tubing Set correctly to the catheter could result in catheter failure. Do not attach the Tubing Set to the dark blue or brown luers.

23. Caution: Do not place any stopcocks in line that may be inadvertently shut off. This can cause line blockage and possible failure.

24. Pump saline through tubing set and catheter to assure that all connections are secure and that there is no leaking. Allow any remaining air in system to be purged out.

25. Set COOLGARD™ pump to a setting of 210.

Disconnecting Catheter from COOLGARD™ System:
1. Stop circulation of saline through catheter.
2. Disconnect Tubing Set from catheter.
3. To maintain sterile connections, immediately cap off luer connectors of both catheter and tubing set using sterile luer caps.

Reconnecting Catheter to COOLGARD™ System:
1. Remove luer caps from luer connectors of catheter and tubing set and discard.
2. Attach Tubing Set to COOL LINE™ Heat Exchange Catheter by connecting the male liter of the Tubing Set to the female inflow luer of the COOL LINE™ catheter and the female luer of the Tubing Set to the male outflow luer of the COOL LINE™ catheter. Assure that a sufficient amount of sterile saline is present at the ends of the hubs make an air free connection.
3. Warning: Failure to connect the tubing set correctly to the catheter could result in catheter failure.
4. Caution: Do not place any extra stopcocks in line that may be inadvertently shut off. This can cause line blockage and possible failure.

Catheter Removal:
1. Stop all pumping of saline through the catheter.
2. Disconnect Tubing Set from catheter.
3. Place patient in supine position. Remove dressing. Remove sutures from suture site.
4. Slowly remove catheter from patient. As catheter exits the site apply pressure with a dressing impermeable to air, e.g. vaseline gauze.
5. Warning: Do not move catheter if resistance is felt. If resistance is encountered, an x-ray should be performed to identify the reason for the resistance.

Sterility

Ethylene oxide sterilized. The COOL LINE™ Catheter is supplied sterile for single use only and should not be resterilized. The package should be inspected prior to use to ensure that the sterility harrier has not been compromised.

Storage

Store at room temperature, 15-40° C.

The above are exemplary modes of carrying out the invention and are not intended to be limiting. It will be apparent to one of ordinary skill in the art that modifications thereto can be made without inventive departure from the spirit and scope of the invention as set forth in the following claims.

The invention claimed is:

1. An apparatus for delivery of thermal treatment to a selected area in the vascular system of a patient, comprising:
   a catheter assembly;
   at least two heat transfer elements on a distal portion of the catheter assembly and configured to be inserted to the selected area in the vascular system;
   a supply lumen communicating with the heat transfer elements to supply a heat exchange fluid to the heat transfer elements;
   a return lumen in the catheter assembly and communicating with the heat transfer elements to receive the heat exchange fluid from the heat transfer elements;
   at least one exit port in the distal portion of the catheter assembly; and
   a through lumen within the catheter assembly extending to the distal portion of the catheter assembly to establish communication through the assembly from the distal portion of said catheter assembly, the exit port being in communication with the through lumen to establish a path for communication from outside the assembly, through the exit port, and into the through lumen.

2. The apparatus of claim 1, wherein fluid communication is established between the supply lumen and at least one of the heat transfer elements by at least one input port and fluid communication is established between the supply lumen and at least one of the heat transfer elements by at least one output port, the output port being larger than the input port.

3. The apparatus of claim 1, further comprising a patient anchor on the assembly and configured for affixing to a patient's skin.

4. The apparatus of claim 2, further comprising a patient anchor on the assembly and configured for affixing to a patient's skin.

5. A method for delivery of thermal treatment to a selected area in the vascular system of a patient, comprising:
  advancing a catheter assembly with at least two heat transfer elements on a distal portion of the catheter assembly to the selected area in the vascular system;
  supplying a heat exchange fluid to the heat transfer elements;
  receiving the heat exchange fluid from the heat transfer elements; and
  using at least one exit port in the distal portion of the catheter assembly to infuse medicament into the patient and/or to withdraw fluid from the patient.

6. The method of claim 5, further comprising:
  using a through lumen within the catheter assembly extending to the distal portion of the catheter assembly to establish communication through the assembly from the distal portion of said catheter assembly, the exit port being in communication with the through lumen to establish a path for communication from outside the assembly, through the exit port, and into the through lumen.

7. The method of claim 5, comprising establishing communication between the supply lumen and at least one of the heat transfer elements by at least one input port and fluid communication is established between the supply lumen and at least one of the heat transfer elements by at least one output port, the output port being larger than the input port.

8. The method of claim 5, further comprising affixing a patient anchor on the assembly to a patient's skin.

* * * * *